United States Patent
Sgro

[19]

[11] Patent Number: 6,063,112
[45] Date of Patent: May 16, 2000

[54] KIT FOR SURGICAL TREATMENT OF INTRACORPOREAL LUMENS

[75] Inventor: Jean-Claude Sgro, Dijon, France

[73] Assignee: Sofradim Production, Villefranche sur Saone, France

[21] Appl. No.: 09/091,835

[22] PCT Filed: Dec. 19, 1996

[86] PCT No.: PCT/IB96/01465

§ 371 Date: Sep. 11, 1998

§ 102(e) Date: Sep. 11, 1998

[87] PCT Pub. No.: WO97/24080

PCT Pub. Date: Jul. 10, 1997

[30] Foreign Application Priority Data

Dec. 28, 1995 [FR] France .................................. 95 15840

[51] Int. Cl.[7] .......................................................... A61F 2/06
[52] U.S. Cl. ........................................................................ 623/1
[58] Field of Search .................................................. 623/1, 12

[56] References Cited

U.S. PATENT DOCUMENTS

| | | | |
|---|---|---|---|
| 5,116,318 | 5/1992 | Hillstead | 604/96 |
| 5,403,341 | 4/1995 | Solar | 623/1 |
| 5,908,448 | 6/1999 | Roberts | 623/1 |
| 5,928,279 | 7/1999 | Shannon | 623/1 |
| 5,941,908 | 8/1999 | Goldsteen | 623/1 |
| 5,948,191 | 9/1999 | Solovay | 623/1 |

FOREIGN PATENT DOCUMENTS 0 686 379A2 12/1995 European Pat. Off. .
0 689 805A2 1/1996 European Pat. Off. .

*Primary Examiner*—Michael J. Milano
*Attorney, Agent, or Firm*—Arent Fox Kintner; Plotkin & Kahn PLLC

[57] ABSTRACT

A treatment kit having an intraluminal prosthesis that treats an intracorporeal lumen. The kit includes, in addition to the expandable prosthesis, a catheter that is introduced inside the lumen. A radially expanding device and an envelope surround the prosthesis when the prosthesis is in a contracted configuration. Two extremities of the envelope are attached to form a single unit with the catheter. The envelope incorporates a flexible sheath that can form a compressed configuration and an extended configuration. The sheath comes into external contact with an internal wall of the intracorporal lumen and detaches itself from the remainder of the envelope.

13 Claims, 4 Drawing Sheets

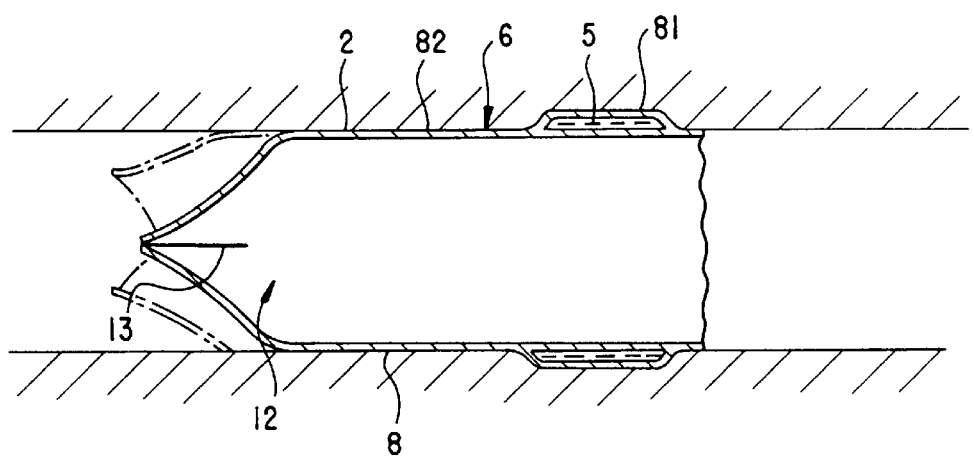

KIT FOR SURGICAL TREATMENT OF INTRACORPOREAL LUMENS

BACKGROUND OF THE INVENTION

The present invention relates to the treatment of an intracorporeal lumen, by applying or fitting an intraluminal prosthesis, or endoprosthesis, in said corporeal lumen, for example in an artery or a vein, in the field of angiology. More particularly, the invention relates to a surgical treatment assembly which facilitates the positioning of a vascular endoprosthesis in a blood vessel.

According to the methods commonly used in vascular surgery, the fitting of vascular endoprostheses or the like requires the use of an application device. For example, the techniques for introducing and applying endoprostheses, either expandable using a balloon or autoexpansible, are generally well known.

In the case of an expandable endoprosthesis, it is generally presented in its retracted configuration, on and around an inflatable balloon, introduced intravenously or intra-arterially with the balloon, and thus brought to the site of the lesion or obstruction to be treated. In this position, the balloon is then inflated in order to bring the endoprosthesis into its deployed configuration, and thus treat the lesion or obstruction. The problems often encountered with a system of this type are due to the endoprosthesis being held poorly on the balloon, in particular resulting in the endoprosthesis being detached from the balloon, or premature release of the endoprosthesis which may result in it being positioned incorrectly, as well as the possibility of the balloon being punctured by one of the ends of the prosthesis, which is often made of metal.

In the case of an autoexpansible endoprosthesis, generally consisting of a shape-memory material, it is often introduced into the vein or artery in two concentric tubes which overlap, and therefore in its retracted configuration, and withdrawal of the tube releases the endoprosthesis with the result that it expands into the deployed configuration.

In order to prevent any displacement of an expandable endoprosthesis along its intra-arterial or intravenous route to the site where it is installed, it is known to use folds of flexible plastic, arranged at the front and rear of the balloon, with the circular edges of the intraluminal prosthesis having previously been slid under these folds, so that it is held by them and cannot be displaced forward or backward. When the balloon is inflated, its radial expansion, and consequently the radial expansion of the endoprosthesis, causes the latter to shorten longitudinally and allows it to detach from the balloon. However, this solution does not make it possible to control the application of all types of intraluminal prostheses, and in particular cannot be applied to autoexpansible endoprostheses.

Another solution has been provided by document WO-A-95/07667, which describes a detachable and hardenable balloon combining the act of angioplasty and the fitting of an internal sheath, which then acts as a stent. The chemical hardening is brought about by applying heat or light, once the balloon has been put in place and inflated, and it is released by the chemical degradation of separation zones consisting of polymers different than those constituting the rest of the balloon. However, this solution does not permit straightforward control of the positioning of the stent balloon, because the chemical degradation and hardening conditions which need to be applied may lead to uncontrolled release of degradation products which are potentially toxic at the local or systemic level.

There has therefore been the need to find an assembly for treating an intracorporeal lumen which includes all the components needed for this treatment in a compact form, these being "packaged" in some way so that they can be deployed with precision and without risk to the patient, in a straightforward and controllable fashion.

BRIEF SUMMARY OF THE INVENTION

The present invention achieves this object by providing an assembly for the treatment of an intracorporeal lumen, making it possible to introduce and position an endoprosthesis in a manner which is both reliable and straightforward.

A treatment assembly according to the invention therefore comprises:

the intraluminal prosthesis, or endoprosthesis, generally of tubular shape and capable of adopting two configurations, namely a retracted one of relatively small internal cross section, and a deployed one of relatively large internal cross section; this prosthesis may be either expandable under the action of a specific additional means, or autoexpansible;

filamentous or elongate means for introducing the prosthesis into the corporeal lumen, for example of the catheter type;

radial expansion means, for example an inflatable balloon, arranged at a distal end of the aforementioned introduction means, between the latter and the prosthesis in its retracted configuration, these means being designed to control, that is to say cause or accompany, the transition of the prosthesis from its retracted configuration to its deployed configuration; these means are actuated at a proximal end of the aforementioned introduction means, so as to be activated or deactivated under the control of the user or manipulator;

and an envelope which surrounds the prosthesis in its retracted configuration.

According to the invention, the envelope is gathered and secured, directly or indirectly, at least at one end, to the introduction means, for example of the catheter type. This envelope has a flexible sheath which extends longitudinally along the axis of the prosthesis, surrounds the latter over at least part of its length, and can adopt two configurations, a contracted one corresponding to the retracted configuration of the prosthesis, and an extended one, coming into external contact with the internal wall of the intracorporeal lumen which is treated, and corresponding to and limiting the deployed configuration of the prosthesis; the transition from the contracted configuration to the extended configuration of the sheath takes place under the effect of the transition of the said prosthesis from its retracted configuration to its deployed configuration, and the envelope incorporates mechanical means for separating the sheath, in its extended configuration, from at least one end of the said envelope.

When the prosthesis is in the deployed configuration, corresponding to the extended configuration of the sheath, the latter is arranged between, on the inside, the prosthesis proper and, on the outside, the wall of the corporeal lumen which is being treated. In this way, the orifices, openings or mesh apertures of the endoprosthesis are closed off by the sheath in its extended configuration, which prevents any proliferation of the cell layer inside the intracorporeal lumen, referred to as intimal hyperplasia in the case of an artery, and consequently any obliteration of the endoprosthesis, because the proliferating cells cannot pass through the mesh apertures or openings of the endoprosthesis. This is an essential yet unexpected advantage of a surgical treatment assembly according to the invention.

Further, in its extended configuration, the sheath affords some degree of protection to the wall of the intracorporeal lumen from the endoprosthesis.

BRIEF DESCRIPTION OF DETAILED DRAWINGS

The present invention will now be described in more detail with reference to the appended drawing, in which:

FIG. 17 is a sectional view of the treatment assembly according to FIGS. 15 and 16, in place in an intracorporeal lumen, after the radial expansion means have been deactivated and withdrawn with the introduction means.

DETAILED DESCRIPTION OF PREFERRED EMBODIMENTS

An assembly 1 according to the invention for the surgical treatment of an intracorporeal lumen 2 will now be described with reference to FIGS. 1 to 7.

Figure 1:
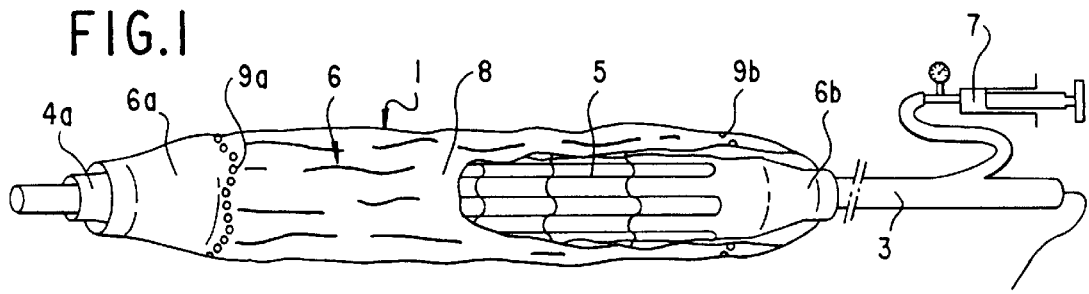
FIG. 1 represents a perspective view, with partial cutaway, of an assembly according to the invention for treating an intracorporeal lumen, before it is introduced into said lumen, and before the radial expansion means are actuated.
Figure 3:
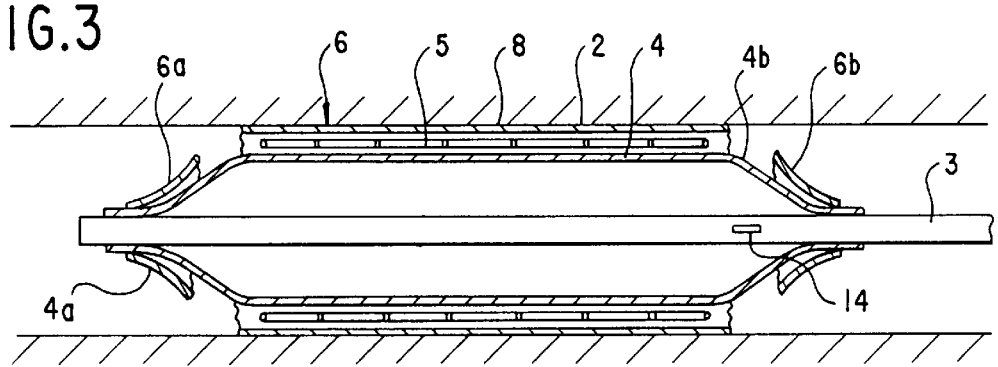
FIG. 3 represents a view in axial section of the assembly according to FIG. 2, showing its various elements.
Figure 4:
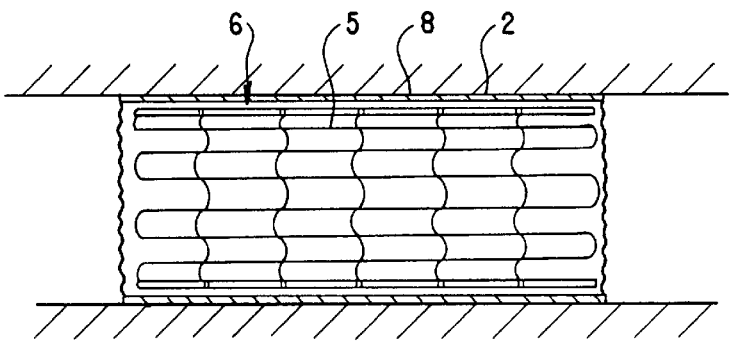
FIG. 4 represents a sectional view of the prosthesis in the deployed state according to FIG. 3, after the radial expansion means have been deactivated and withdrawn with the introduction means.
Figure 5:
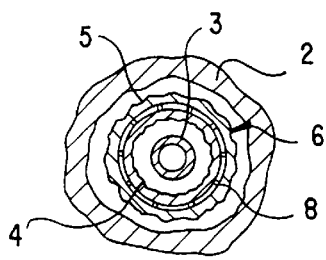
FIG. 5 represents a cross-sectional view of an intracorporeal lumen which is being treated, and into which the assembly according to FIG. 1 has been introduced, before the radial expansion means are actuated.
Figure 6:
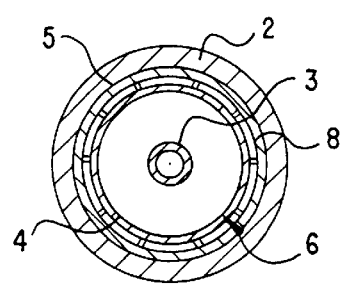
FIG. 6 is a similar view to FIG. 5, showing the assembly according to FIG. 2 after the radial expansion means have been actuated.
Figure 7:
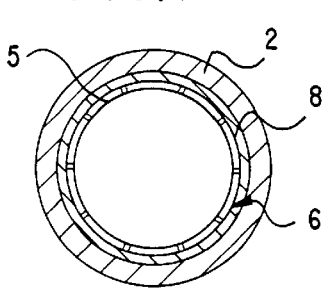
FIG. 7 is another view similar to the one in FIG. 6, once the introduction and radial expansion means have been withdrawn.

An assembly 1 according to the invention comprises:

an expandable or autoexpansible intraluminal prosthesis 5 of the traditional type, generally in tubular form and made or obtained from, for example, a biocompatible wire; this prosthesis 5 can adopt two configurations, namely a retracted one, shown in FIGS. 1 and 5, of relatively small internal cross section, and a deployed one, shown in FIGS. 2 to 4 and 6 and 7, of relatively large internal cross section;

filamentous or elongate means 3 for introducing the prosthesis 5 into the corporeal lumen 2; according to FIG. 1, these means are for example a traditional catheter, also permitting endoscopy;

radial expansion means 4, arranged at a distal end of the introduction means 3, between them and the prosthesis 5 in its retracted configuration, and designed to control, as described below, the transition of the prosthesis 5 from its retracted configuration to its deployed configuration; these are, as represented in FIG. 3, an inflatable balloon whose two ends 4a and 4b are secured in leaktight fashion on the introduction means 3, in this case the catheter;

means 7 for actuating the radial expansion means 4, arranged at a proximal end of the introduction means 3, as is represented in FIG. 1; in traditional fashion, these means 7 consist of a pump, of the syringe type, making it possible to inject a gas or liquid into the inflatable balloon 4 through the orifice 14 shown in FIG. 3; the same actuation means make it possible, in the reverse procedure, to extract the liquid or gas from the balloon 4;

and an envelope 6 which surrounds the prosthesis 5 in its retracted configuration.

According to the invention, the envelope 6 is firstly gathered and secured at its two ends 6a and 6b, respectively, to the introduction means 3, in this case the catheter; this securing is carried out either directly in contact with the catheter 3, or on the two ends 4a and 4b of the balloon 4, themselves secured in leaktight fashion to the catheter 3.

Next, the envelope 6 has a flexible sheath 8 which extends longitudinally along the axis of the prosthesis 5, surrounds the latter over at least a part of its length in the case in point all of its length, and can adopt two configurations, a contracted one, shown in FIGS. 1 and 5, corresponding to the retracted configuration of the prosthesis 5, and an extended one, shown in FIGS. 2 to 4, and 6 and 7, coming into external contact with the internal wall of the intracorporeal lumen 2, and corresponding to and limiting the deployed configuration of the prosthesis 5. The transition from the contracted configuration to the extended configuration of the sheath 8 is brought about under the effect of the transition of the prosthesis 5 from its retracted configuration to its deployed configuration.

Lastly, the envelope 6 incorporates mechanical means 9a and 9b for separating the sheath 8, in its extended configuration, from the two ends 6a and 6b, respectively, of the envelope 6.

At least the part of the envelope 6 forming the sheath 8 is in the form of a flexible wall, gathered in its contracted configuration by longitudinal folds parallel to the axis of the prosthesis 5. At least the part of the envelope 6 forming this sheath 8 is obtained in the form of a permeable continuous wall, for example in the form of a fabric, a film or a cloth, made of at least one optionally absorbable biocompatible and/or hemocompatible material, in particular PTFE, polyurethane, polyester, polyamide, polypropylene, collagen or polymers derived from hyaluronic and/or lactic acid.

When the prosthesis 5 is expandable under the effect of the radial expansion means 4, then the sheath 8, when it is in the contracted configuration, remains free relative to the prosthesis 5, itself in its retracted configuration.

When the prosthesis 5 is autoexpansible, then two alternatives may be adopted as regards the sheath 8:

either the sheath 8, when it is in the contracted configuration, is strong enough to contain the return centrifugal autoexpansion of the prosthesis 5, itself in its retracted configuration, but not strong enough to additionally counter the centrifugal radial force of the radial expansion means 4 when activated by the actuation means 7;

or the part of the envelope 6 forming the sheath 8 is obtained from an elastic or viscoelastic material which initially has a thickness sufficient to contain the return centrifugal autoexpansion of the prosthesis 5, itself in its retracted configuration, then can become thinner under the effect of the centrifugal radial force exerted by the radial expansion means 4, thus releasing the centrifugal autoexpansion of the prosthesis 5 into its deployed configuration.

Figure 2:
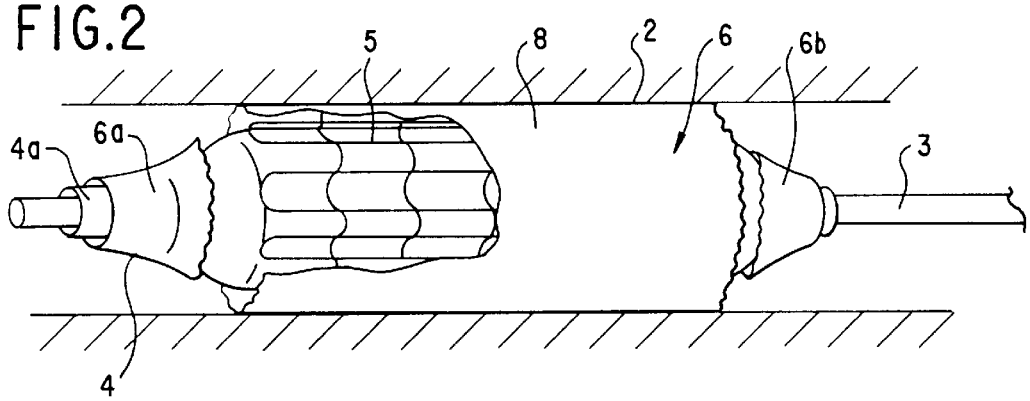
FIG. 2 represents a perspective view, with partial cutaway, of the assembly according to FIG. 1 after introduction into the corporeal lumen, at the site of the desired treatment, and after actuation of the radial expansion means.

According to the representation in FIG. 1, the mechanical separation means 9a and 9b consist of or comprise two closed mechanically weak lines, each having an alternate zigzag shape, extending generally along two circumferences or bands, respectively concentric with the axis of the prosthesis 5. These two separation means, or weak lines, for example in the form of "dashed" precuts, which are formed in the wall or material of the envelope 6 are arranged on either side of the sheath 8. Under the mechanical effect of the radial expansion of the envelope 6, in contact with the prosthesis 5 which is itself undergoing radial expansion, these two weak lines 9a and 9b form two lines of full separation, as shown by FIG. 2, when the sheath 8 consequently changes from its contracted configuration to its extended configuration.

Figure 8:
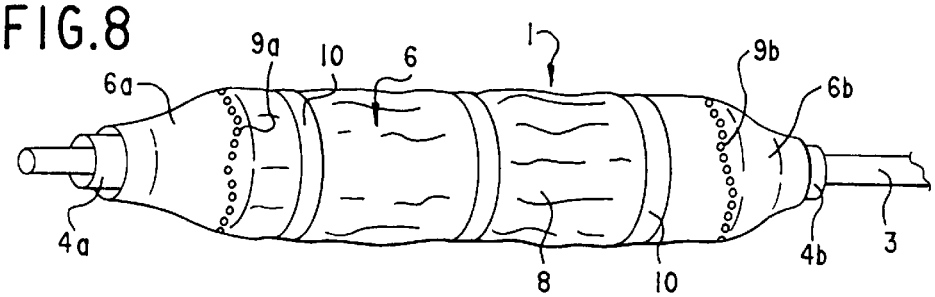
FIG. 8 is a perspective view of a first variant of a treatment assembly according to the invention, before it is introduced into the intracorporeal lumen and the radial expansion means are actuated.
Figure 9:
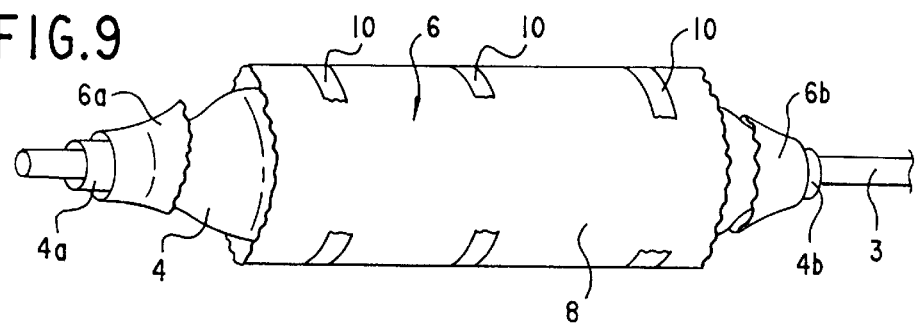
FIG. 9 is a perspective view of the assembly according to FIG. 8, after actuation of the radial expansion means, this of course taking place in the intracorporeal lumen which is being treated, although the latter has not been represented.

The first variant of the assembly described above differs from the latter in that, with reference to FIGS. 8 and 9, optionally closed circumferential bands 10 are attached and distributed over the sheath 8, and are designed to contain with said sheath the return centrifugal autoexpansion of the prosthesis 5, as well as to break under the additional centrifugal radial force exerted by the radial expansion means 4, when the latter are activated. The same bands may be incorporated in some way in the wall of the sheath 8.

Figure 10:
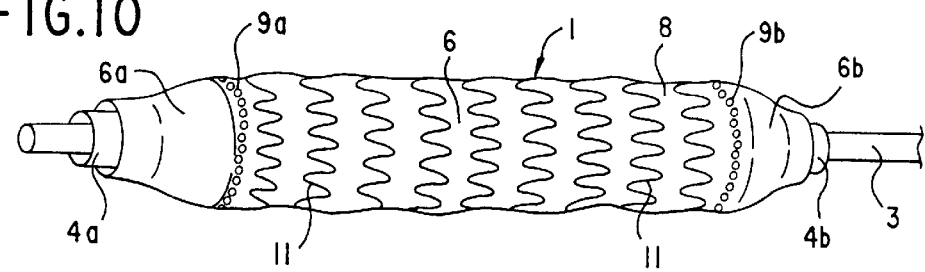
FIG. 10 is a perspective view of a second variant of an assembly according to the invention, before the radial expansion means are actuated.
Figure 11:
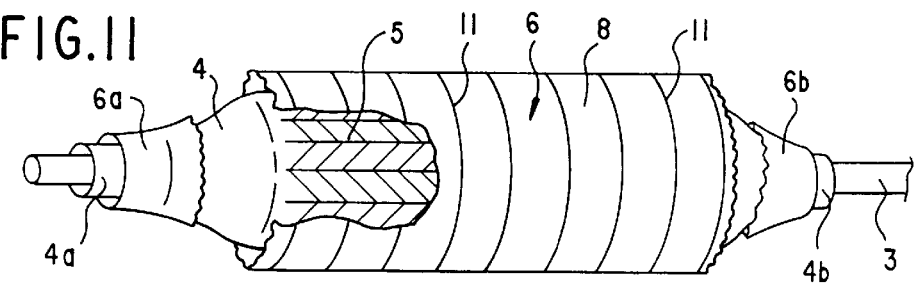
FIG. 11 is a perspective view of the assembly according to FIG. 10, after actuation of the radial expansion means.
Figure 12:
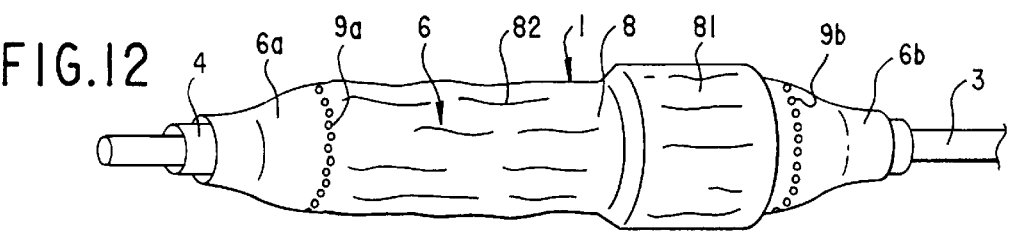
FIG. 12 is a perspective view of a third variant of the treatment assembly according to the invention, before the radial expansion means are actuated.
Figure 13:
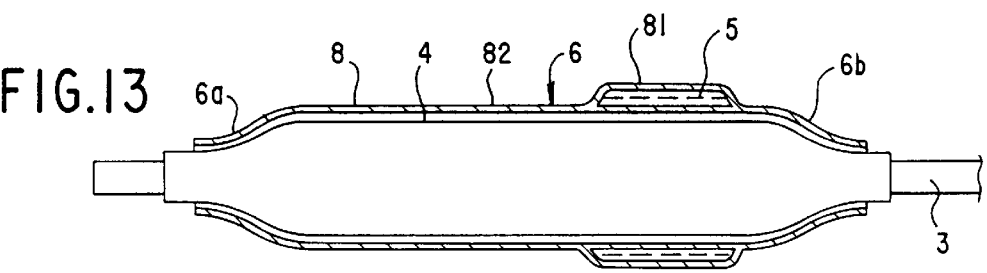
FIG. 13 is a view in axial section of the treatment assembly represented in FIG. 12, before the radial expansion means are actuated.
Figure 14:
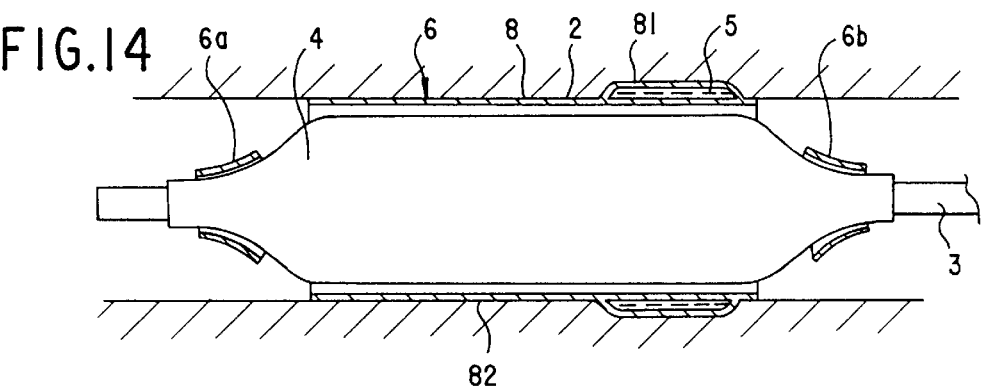
FIG. 14 is a view in axial section of the treatment assembly represented in FIG. 12, after introduction into a corporeal lumen and actuation of the radial expansion means.

According to the second variant of the assembly according to the invention, which is represented in FIGS. 10 and 11, the sheath 8 incorporates means 11 for stopping its own extension, these means being arranged in the folded state (cf. FIG. 10) when said sheath is in the contracted configuration, and in the unfolded state (cf. FIG. 11) when the sheath 8 is in the extended configuration. In the unfolded state, when the sheath 8 is in the extended configuration, the stop means 11 are designed or chosen so as to withstand any centrifugal thrust, for example exerted by an autoexpansible endoprosthesis, beyond or greater than that necessary for or due to the transition of the prosthesis 5 from its retracted configuration to its deployed configuration. As represented in FIGS. 10 and 11, these stop means 11 consist of threads, or any other filamentous means, in particular fibers, arranged circumferentally in continuous fashion and consisting of at least one mechanically strong material, in particular polyester, polyurethane or polypropylene. In the folded state, each of these threads has an alternate zigzag shape, and each of these threads adopts a circular shape in the unfolded state.

This second variant can be used to treat aneurysmal regions, that is to say dilated regions with a very fragile wall, since it makes it possible to limit the extension of the sheath 8. In particular, the expansion of the balloon 4 encounters the resistance exerted by the stop means 11, in the unfolded state, which also prevents any continuation of the extension of the sheath 8 under the effect of blood pressure, in the case of a vascular surgical treatment.

The third variant of the assembly according to the invention, which is represented with reference to FIGS. 12 to 17, is characterized in that the sheath 8 comprises two parts, namely a first part 81 which surrounds the prosthesis 5, and a second part 82, which is not absorbable, which is arranged both to form a valve 12, when the sheath 8 is in the extended configuration, and remained [sic] free in this form inside the intra-corporeal lumen 2 which is being treated. When the sheath 8 is in the extended configuration, the second part 82 optionally has a cross section smaller than that of the cross section of the first part 81, when the sheath 8 is in the extended configuration; this smaller cross section actually decreases conically from the first part 81 to the end opposite it.

Figure 15:
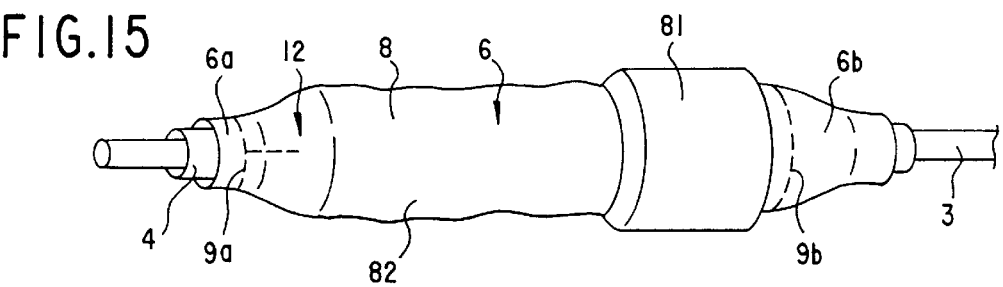
FIG. 15 is a perspective view of a preferred modification to a treatment assembly according to FIGS. 12 to 14, after actuation of the radial expansion means.
Figure 16:
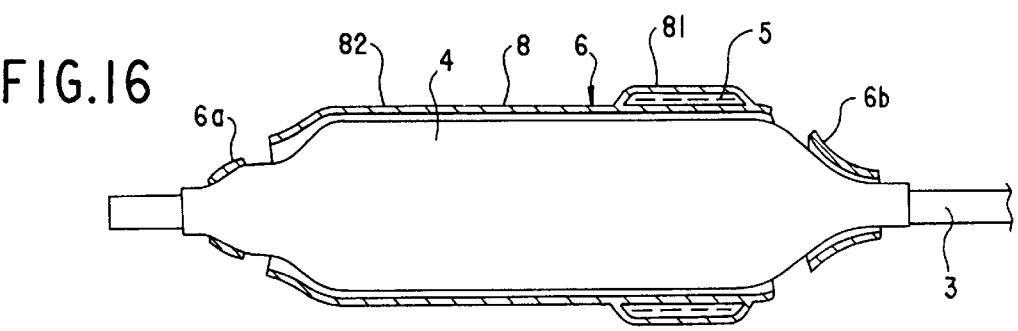
FIG. 16 is a sectional view of the treatment assembly according to FIG. 15, after actuation of the radial expansion means.

When the sheath 8 is in its extended configuration, its second part 82 has two opposite slits 13 parallel to the axis of the prosthesis 5, which are obtained from two corresponding weak lines, represented in FIG. 15 and formed in the second part 82, when the sheath 8 is in the contracted configuration. The two partial weak lines 13 are arranged perpendicular to the weak line 9a, making it possible to separate the sheath 8 from the end 6a of the envelope 6.

Further, the first part 81 actually forms a fold making it possible to enclose the prosthesis 5 fully, as represented by FIGS. 13, 14, 16 and 17.

This third variant makes it possible to add a valve system to the endoprosthesis, capable of being used in the surgical treatment of venous blood vessels, for example. This makes it possible, in particular, to treat the repermeating veins whose valves no longer function, after episodes of intense deep phlebitis, without having to take normal veins from the same individual or patient and fit them surgically instead of the deficient veins. This also makes it possible to treat certain cases of varices due to valve incontinence, while retaining the venous capacity.

According to this variant, the endoprosthesis is essentially used to block the prosthetic valve system in place in the blood vessel.

What is claimed is:

1. Assembly for the treatment of an intracorporeal lumen, comprising:

an intraluminal prosthesis with a substantially tubular shape, said prosthesis having a retracted configuration and a deployed configuration said deployed configuration providing an internal cross section larger than an internal cross section of said retracted configuration;

filamentous introduction means for introducing a catheter into the intracorporeal lumen;

radial expansion means for controlling a transition of said prosthesis from said retracted configuration to said deployed configuration, said radial expansion means being arranged at a distal end of said filamentous introduction means and between said filamentous introduction means and said prosthesis in said retracted configuration, said radial expansion means being actuated at a proximal end of said filamentous introduction means; and an envelope which surrounds said prosthesis in said retracted configuration, wherein said envelope is gathered and secured at least at one end to said filamentous introduction means and has a flexible sheath which extends longitudinally along an axis of said prosthesis and surrounds a portion of length of said prosthesis, said flexible sheath having a contracted configuration corresponding to said retracted configuration of said prothesis and an extended configuration coming into external contact with an internal wall of the intracoporeal lumen, said flexible sheath corresponds to and limits said deployed configuration of said prosthesis, a transition of said flexible sheath from said contracted configuration to said extended configuration taking place under the effect of the transition of said prosthesis from said retracted configuration to said deployed configuration, said envelope incorporates mechanical separation means for separating said flexible sheath in said extended configuration from at least one end of said envelope.

2. Assembly according to claim 1, wherein said mechanical separation means comprise two closed mechanically weak lines which extend along two bands concentric with said axis of said prosthesis, said weak lines being positioned on either side of said sheath and form two lines of full separation when said sheath changes from said contracted configuration to said extended configuration.

3. Assembly according to claim 1, wherein at least the part of the envelope forming the sheath is formed from one of a fabric, a film and a cloth of either one of an absorbable biocompatible and hemocompatible material selected from a group including PTFE, polyurethane, polyester, polyamide, polypropylene, collagen and polymers derived from either one of a hyaluronic and lactic acid.

4. Assembly according to claim 1, wherein the prosthesis expands under the effect of the radial expansion means, and when the sheath is in the contracted configuration, the sheath is free relative to the prosthesis, which is in the retracted configuration.

5. Assembly according to claim 1, wherein the prosthesis is autoexpansible, and when the sheath is in the contracted configuration, the sheath contains a return centrifugal autoexpansion of the prosthesis, when the prosthesis is in the retracted configuration.

6. Assembly according to claim 5, further comprising optionally closed circumferential bands attached to the sheath and contain, with said sheath, the return centrifugal autoexpansion of the prosthesis, said optionally closed circumferential bands break under a centrifugal radial force exerted by the radial expansion means.

7. Assembly according to claim 5, wherein at least the part of the envelope forming the sheath is formed from an elastic material initially having a thickness that contains the return centrifugal autoexpansion of the prosthesis when the prosthesis is in the retracted configuration, the thickness of the elastic material thins under the effect of the centrifugal radial force exerted by the radial expansion means, wherein said prosthesis is released into the deployed configuration.

8. Assembly according to claim 1, wherein the sheath includes stopping means for stopping the extension of the sheath in a folded state when said sheath is in the contracted configuration, and in an unfolded state when said sheath is in the extended configuration, wherein during the unfolded state the stopping means withstands any centrifugal thrust beyond that necessary for the transition of the prosthesis from the retracted configuration to the deployed configuration.

9. Assembly according to claim 8, characterized in that the stop means comprise threads, or fibers, or other filamentous means, arranged circumferentially in continuous fashion and made of at least one strong material, in particular polyester, polyurethane or polypropylene.

10. Assembly according to claim 1, wherein the sheath comprises a first part which surrounds the prosthesis and a second part which remains free inside the intracorporeal lumen and, when the sheath is in the extended configuration, the second part has cross section that is smaller than a cross section of the first part.

11. Assembly according to claim 10, wherein the second part of the sheath is not absorbable and forms a valve when the sheath is in the extended configuration.

12. Assembly according to claim 10, wherein the second part of the sheath has, when the sheath is in the extended configuration, a cross section which decreases from the first part of an opposite end.

13. Assembly according to claim 12 the second part of the sheath has, when the sheath is in the extended configuration, two opposite slits which are parallel to the axis of the prosthesis and are formed from two corresponding weak lines arranged in said second part when the sheath is in the contracted configuration.

* * * * *

UNITED STATES PATENT AND TRADEMARK OFFICE
CERTIFICATE OF CORRECTION

PATENT NO. : 6,063,112
DATED : May 16, 2000
INVENTOR(S) : Sgro

Page 1 of 1

It is certified that error appears in the above-identified patent and that said Letters Patent is hereby corrected as shown below:

Item [54], please delete "KIT FOR SURGICAL TREATMENT OF INTRACORPOREAL LUMENS", and insert --KIT FOR SURGICAL TREATMENT OF INTRACORPORAL LUMENS--

Signed and Sealed this

Seventeenth Day of July, 2001

*Attest:*

*Attesting Officer*

NICHOLAS P. GODICI
*Acting Director of the United States Patent and Trademark Office*